United States Patent
DeCarlo, Jr. et al.

(10) Patent No.: US 6,355,069 B1
(45) Date of Patent: *Mar. 12, 2002

(54) BONE ENGAGING PROSTHESIS

(75) Inventors: Alfred F. DeCarlo, Jr., Stamford, CT (US); Hugh U. Cameron, Toronto (CA)

(73) Assignee: Depuys Orthopaedics, Inc., Warsaw, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/137,249

(22) Filed: Aug. 20, 1998

(51) Int. Cl.⁷ .................................................. A61F 2/36
(52) U.S. Cl. .............................. 623/23.26; 623/20.34; 623/20.36; 606/63
(58) Field of Search .......................... 623/18–23, 20.34, 623/20.36, 22.43, 23.26; 606/59–68; 411/77

(56) References Cited

U.S. PATENT DOCUMENTS

| 3,760,802 | A | | 9/1973 | Fischer et al. | .......... 128/92 BC |
| 4,091,806 | A | * | 5/1978 | Aginsky | ........................ 606/67 |
| 4,520,511 | A | | 6/1985 | Gianezio et al. | .............. 3/1.913 |
| 5,314,489 | A | | 5/1994 | Hoffman et al. | ............... 623/22 |
| 5,644,439 | A | | 7/1997 | Shiba | ......................... 359/819 |

FOREIGN PATENT DOCUMENTS

| FR | 0385930 | 9/1990 | ............. A61F/2/36 |
| FR | 2653660 | 5/1991 | ............. A61F/2/36 |
| WO | WO 94/07438 | 4/1997 | |

* cited by examiner

*Primary Examiner*—Bruce Snow
(74) *Attorney, Agent, or Firm*—Nutter, McClennan & Fish, LLP

(57) ABSTRACT

A bone prosthesis is provided which includes an implantable elongate stem member having a bore extending therethrough. The stem member has a proximal end and a distal end with at least one slot formed in the distal end. The slot extends along at least a portion of the stem member, in a longitudinal direction, from the distal end towards the proximal end to form at least two tines at the distal end of the stem. A bolt member is disposed within the bore of the stem member and has a proximal end and a distal end, wherein at least a portion of the bolt member proximate the distal end is threaded. An expander nut is disposed between the tines and is threadably matable with the distal end of the bolt member such that rotation of the bolt member in a first direction is effective to draw the expander nut towards the proximal end of the stem member to separate the tines at the distal end of the stem member.

8 Claims, 5 Drawing Sheets

Bone Engaging Prosthesis

CROSS-REFERENCE TO RELATED APPLICATIONS

Not applicable.

STATEMENT REGARDING FEDERALLY SPONSORED RESEARCH

Not applicable.

FIELD OF THE INVENTION

The invention relates to the field of implantable articles. More particularly, the invention relates to a prosthesis system which has an expandable stem region to secure the prosthesis system within a long bone.

BACKGROUND OF THE INVENTION

Joint replacement surgery is quite common and enables many individuals to function normally when otherwise it would not be possible to do so. Artificial joints are normally composed of metallic and/or ceramic components that are fixed to existing bone closest to the joint being replaced.

Artificial hip joints, for example, include several components. A femoral component of an artificial hip includes an elongate stem or shaft at its distal end that is affixed within the medullary canal of the femur. A proximal end of the stem has a neck region which includes a trunnion, to which is attached a femoral head. The acetabular shell is a separate component of an artificial hip joint that is affixed within existing bone such as the acetabulum. The acetabular shell often includes a cup-like liner that receives the femoral head.

Typically, for a hip joint, the elongate stem or shaft portion of the prosthesis is implanted in the medullary canal of the femur. However, many times the femur or other long bone where the stem portion is to be secured can be in a damaged or weakened condition insufficient to support the prosthesis. In such cases, it may be necessary to use a stem having a length that extends beyond the isthmus or narrow portion of the bone.

However, extending the prosthesis beyond the isthmus poses a conflicting problem since the supporting bone beyond the isthmus both widens and can diverge in more than one plane. A prosthesis stem narrow enough to pass through the isthmus may not have sufficient dimensions to provide a secure fit beyond the isthmus where the supporting cortical bone widens or diverges in more than one plane.

Thus it would be desirable to have a prosthesis system that has a strong and effective support for structurally unsound long bone while still being able to pass through the narrow portion of the long bone.

SUMMARY OF THE INVENTION

The invention provides a modular joint prosthesis which includes an implantable elongate stem member having a bore extending therethrough. The stem member has a proximal end and a distal end with at least one longitudinally oriented slot formed in the distal end. The slot is longitudinally formed in at least a portion of the stem member, and it extends from the distal end towards the proximal end to form at least two tines at the distal end of the stem.

The prosthesis also includes a bolt member that is disposable within the bore of the stem member. The bolt member has a proximal end and a distal end, at least a portion of which is threaded.

An expander nut is disposed between the tines of the prosthesis and it is threadably matable with the distal end of the bolt member. The rotation of the bolt member in a first direction is effective to draw the expander nut towards the proximal end of the stem member to separate the tines, thus expanding the distal end of the stem member. The expander nut may have more than one diameter to spread the tines to different diameters and alternatively, the tines may be provided with varying thicknesses.

DETAILED DESCRIPTION OF THE INVENTION

Figure 1:
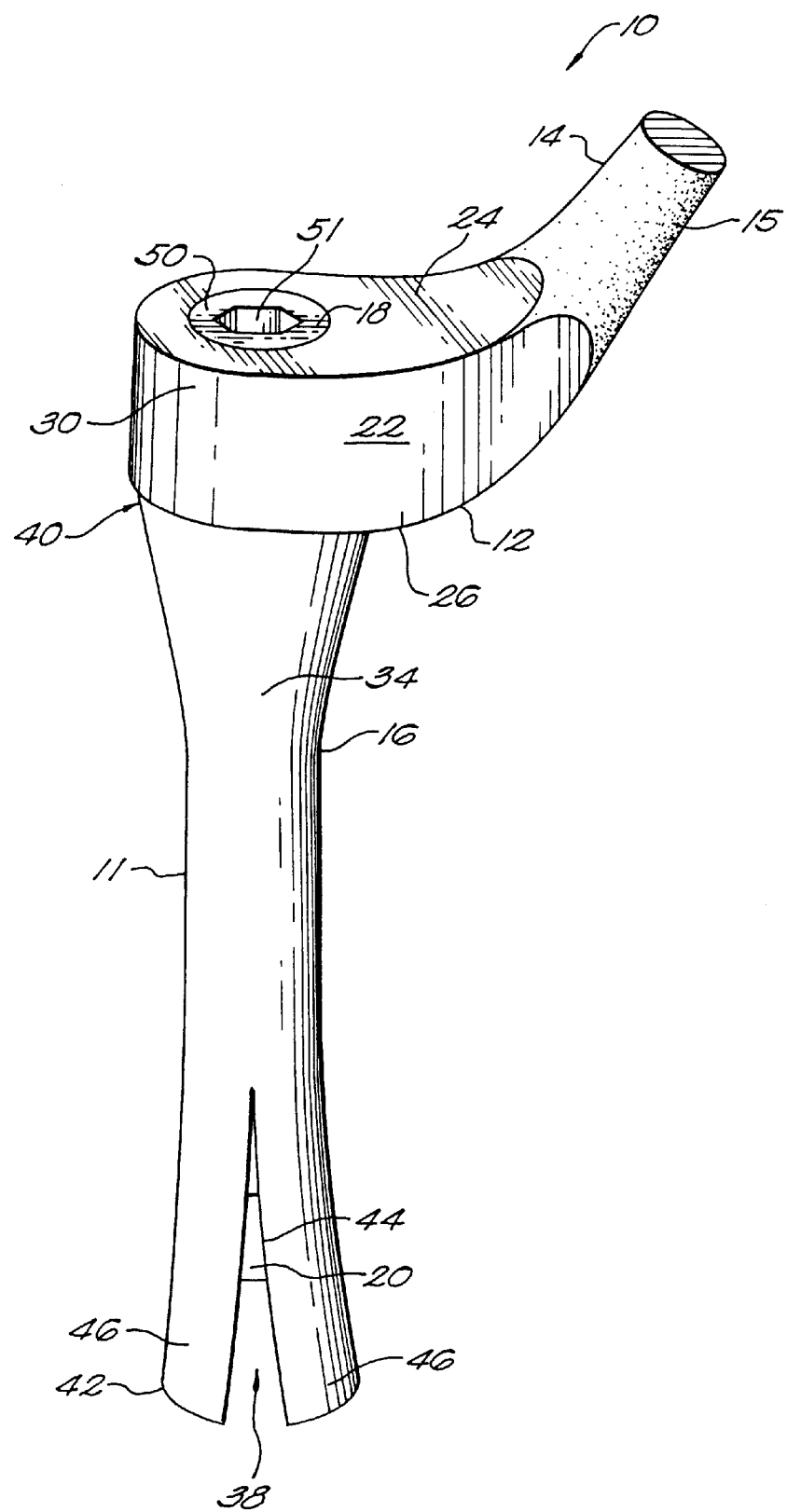
FIG. 1 is a perspective view of a joint prosthesis of the present invention.
Figure 2:
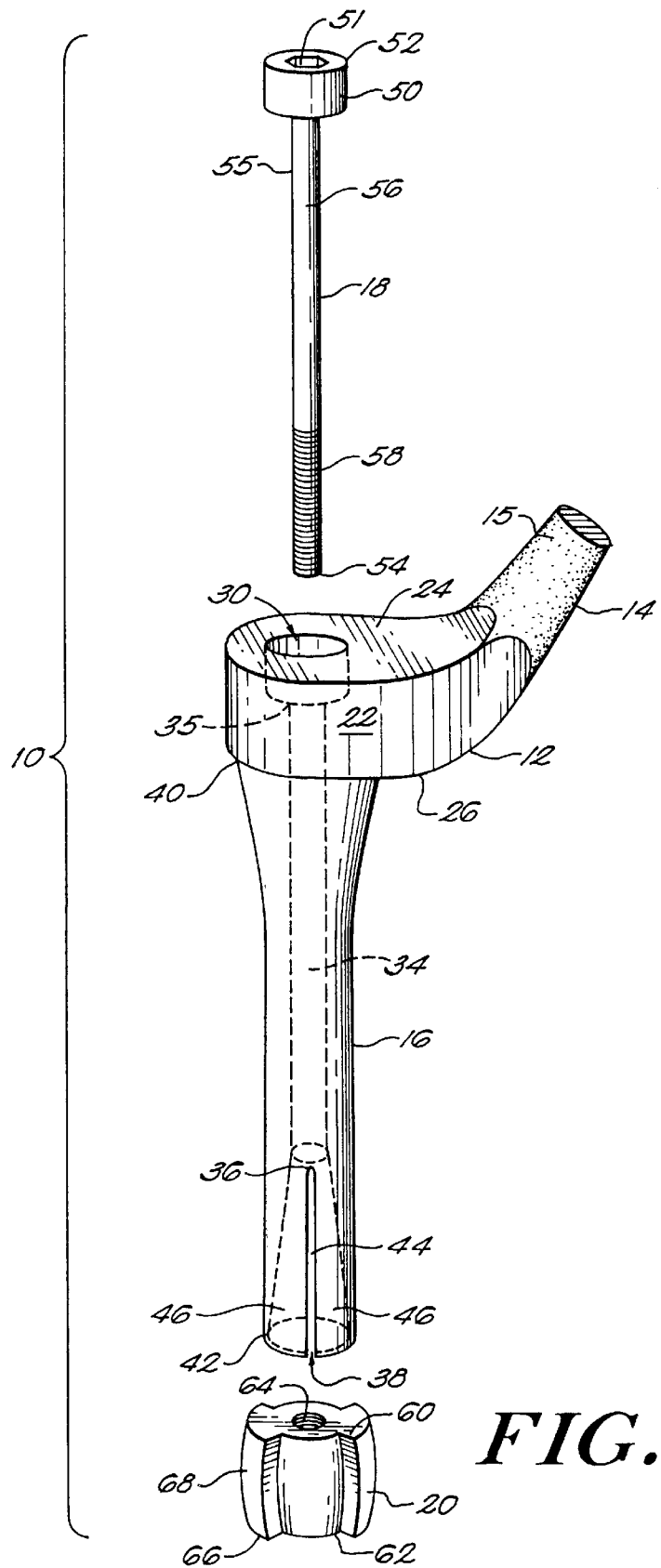
FIG. 2 is an exploded perspective view of the joint prothesis of FIG. 1.
Figure 3:
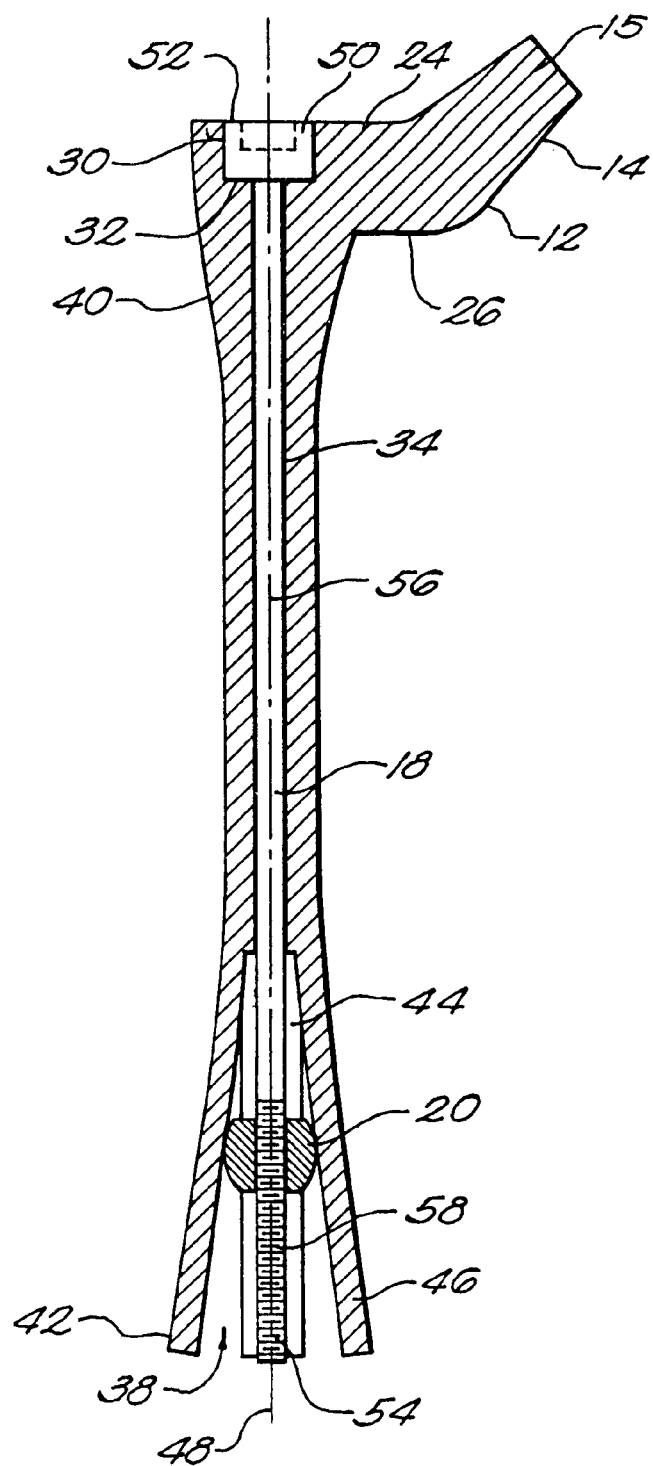
FIG. 3 is a side sectional view of the joint prothesis of FIG. 1 in an expanded condition.

Referring to FIGS. 1 through 3, a joint prothesis component system 10 is provided. The system 10 includes prosthesis 11 with a collar region 12, an elongated stem region 16, a bolt member 18 and an expander nut 20. In the embodiment illustrated and described herein, the joint prosthesis components are shown as femoral components of a hip joint prosthesis system. It is understood, however, that the invention applies to components of other prosthesis systems which require the mounting of a prosthesis to a long bone.

The collar region 12 has a main body 22 which includes a superior surface 24 and an inferior surface 26. A recessed mounting cavity 30 which communicates with bore 34, is provided on the superior surface 24 of the collar 12. The cavity 30 includes a retaining shoulder 32 that prevents a bolt head 50 from sliding further into the stem member 16. Extending from the superior surface 24 is a joint motion surface 14 having a neck portion 15 which has a standard, Morse type taper to allow fixing of a spherical ball, not shown, to the prosthesis. The spherical ball may be either positioned in an acetabular cup, not shown, in the total hip prosthesis or placed directly into the acetabulum to form an endoprosthesis.

Extending distally from the inferior mounting surface 26 of collar 12 is an elongate stem region 16 having a longitudinal axis 48. As illustrated, the stem member 16 has a substantially circular cross section but may also be elliptical, oval, spherical or any other suitable shape to conform to the bone in which the prosthesis is to be implanted. Stem member 16 has a proximal end 40 and a distal end 42 with at least one longitudinal slot 44 formed in the distal end 42. The slot 44 extends in a direction from the distal end 42 towards the proximal end 40 of stem member 16 to form at least two expandable tine members 46. Preferably, the at least one slot 44 has a length in the range of 4 to 10 cm. It is contemplated that more than one slot may be used to form more than two tine members.

The prosthesis further includes a central bore 34, coaxial with longitudinal axis 48, which has proximal and distal ends 35, 36. The bore 34 extends longitudinally from within the mounting cavity 30 and merges into a tapered open tine cavity 38. Preferably, the bore 34 maintains a uniform diameter in the range of 4 to 9 mm, which should be less than the diameter of open tine cavity 38. In an exemplary embodiment, tine cavity 38 has a conical taper with a diameter which ranges from 6 to 14 mm at one end proximate the distal end 36 of bore 34 and 8 to 18 mm proximate the distal end 42 of stem member 16. The conical bore 34 generally has an initial diameter which is less than a minor diameter of expander nut 20 and a diameter at the distal end 42 greater than or equal to a major diameter of expander nut 20, as discussed in more detail later herein.

Referring to FIGS. 2 through 4B, the system 10 further includes an elongate bolt member 18 having a proximal end 52 and a distal end 54. The bolt member 18 includes a head portion 50 and a shaft portion 55 that extends distally from the head portion 50. The shaft portion 55 preferably includes both an unthreaded shaft portion 56 disposed adjacent to the head portion 50, and a lower, threaded portion 58 disposed adjacent to the unthreaded portion 56. The unthreaded shaft portion 56 preferably has an outer diameter that is less than the outer diameter of the head portion 50. The lower, threaded portion 58 preferably has a diameter less than or equal to the diameter of the unthreaded portion 56. The bolt member 18 is disposable within bore 34 of stem member 16 in the manner discussed below.

The bolt member 18 is illustrated with a bolt head opening 51 having six flattened sides suitable for engaging a hex allen-type wrench. However, the bolt head 50 can be provided with other configurations known to those having ordinary skill in the art to permit the bolt member 18 to be tightened or loosened with a tool or by hand when coupled to the expander nut 20.

Referring to FIGS. 2–5B, the expander nut 20 includes a superior surface 60 and an inferior surface 62 with a threaded center bore 64 extending from the superior surface 60 to the inferior surface 62. When properly positioned in the prothesis, the threaded center bore 64 is coaxial with the longitudinal axis 48 of stem member 16. The expander nut 20 further includes at least one anti-rotation means or rotation inhibiting projection 66 and at least one pair of opposed tine engaging side walls 68 adjacent to the at least one rotation inhibiting projection 66. The tine engaging sidewalls 68 are adapted to matingly engage an inner mating surface 47 of tine members 46 when the expander nut 20 is threadably mated to the bolt member 18. In one embodiment, the tine engaging sidewalls 68 may be slightly curved in the longitudinal direction to promote smooth contact with the inner mating surface 47 of tine members 46. In operation, the tine engaging sidewalls 68 cooperate with the rotation inhibiting projection 66 to expand tine members 46 when bolt member 18 is turned.

In an exemplary embodiment, the components of the prosthesis system can be assembled in the following manner.

The bolt member 18 is first positioned, distal end first, into mounting cavity 30 and positioned such that the head portion 50 is recessed within the cavity 30 and the bolt shaft 55 extends into bore 34. The expander nut 20 then is positioned proximate the distal end 42 of stem member 16 and the rotating inhibiting projections 66 are aligned with slots 44 on the stem member 16. The expander nut 20 and bolt member 18 are then joined by mechanical interaction of the threads of bolt shaft 55 with the center bore 64 of expander nut 20 to form a secure prosthesis assembly. As assembled, the prosthesis system may now be implanted in a patient and expanded to a desired configuration.

Referring to FIGS. 4A, 4B, 5A and 5B, the rotation of the bolt member 18 in a first direction, typically clockwise, is effective to draw or urge the expander nut 20 towards the proximal end 40 of stem member 16. As the bolt member 18 is rotated, the tine engaging sidewalls 68 are brought into contact with inner mating surface 47 of tine members 46. As the expander nut 20 is urged upwardly in the tapered tine cavity 38, engaging sidewalls 68 press against the inner mating surfaces 47 causing tine members 46 to be pushed outwardly in a direction generally transverse to the longitudinal axis 48 of stem member 16. The prosthesis may be further adjusted by either tightening or loosening bolt member 18, thereby enabling the expander nut 20 to move longitudinally in a direction towards or away from the proximal end 40 of the stem member 16.

Figure 4A:
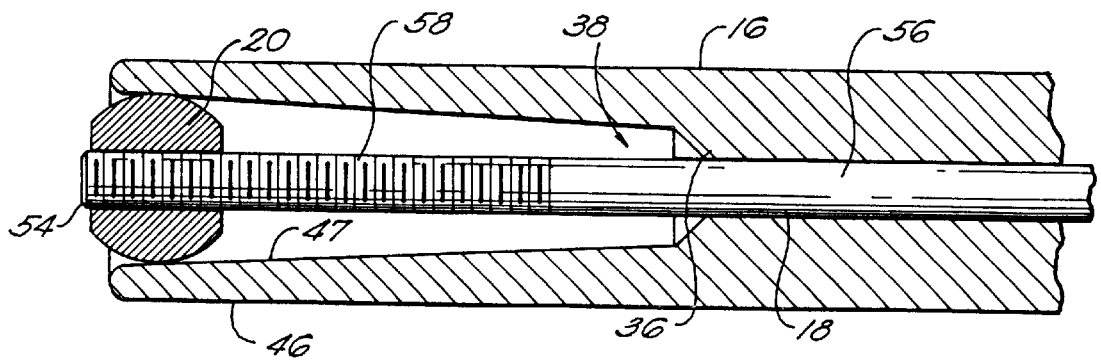
FIG. 4A is a detailed sectional view of the distal portion of the joint prothesis of the present invention in an unexpanded condition.
Figure 4B:
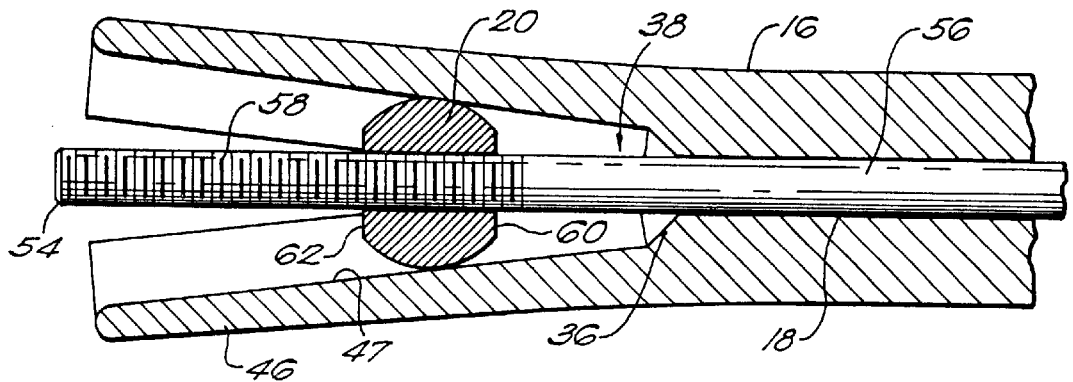
FIG. 4B is a detailed sectional view of the distal portion of the joint prothesis of the present invention in an expanded condition.
Figure 5A:
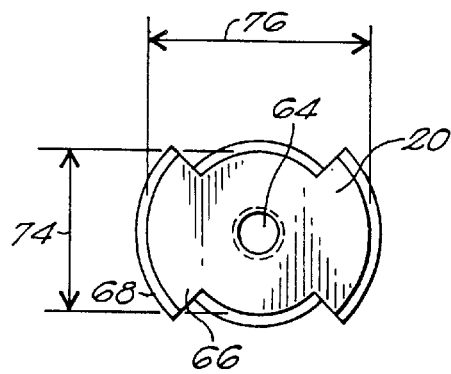
FIG. 5A is a bottom view of the joint prosthesis of FIG. 4A in an unexpanded condition.

In an unexpanded condition as shown in FIGS. 4A and 5A, the prosthesis can be first passed through a narrow section of bone, such as the isthmus of a femur. Once the prosthesis is inserted past the isthmus, the bolt member may be turned to expand the tine members to fill the bone area where the supporting cortical bone is diverging. Once the desired expansion of the prosthesis is achieved, the prosthesis will be secured in place in the long bone.

Figure 5B:
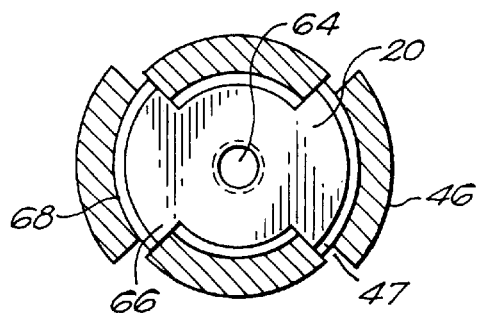
FIG. 5B is a bottom view of the joint prosthesis of FIG. 4A in an expanded condition.

In the embodiment shown in FIGS. 5A and 5B, the prosthesis includes an expander nut 20 having more than one diameter effective to spread adjacent tine members in a non-uniform fashion with respect to one another. The expander nut 20 includes a minor diameter 74, measured in a first direction, which is preferably in the range of about 8 to 16 mm. The expander nut 20 also includes a major diameter 76, measured in a second direction substantially transverse to the minor diameter 74, which is preferably in the range of about 10 to 18 mm. As so configured, the tine members which are positioned about the major diameter 76 can be expanded to a greater relative distance than the tine members which are positioned about the minor diameter 74.

Figure 6A:
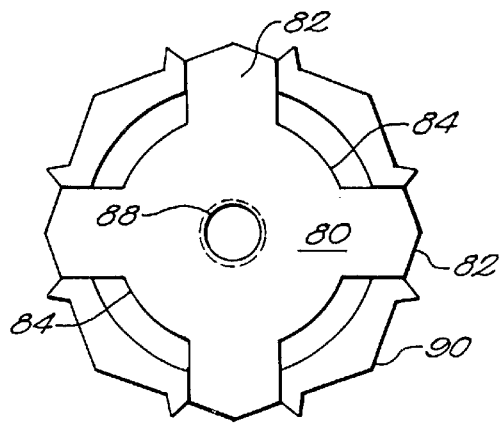
FIG. 6A is a bottom view of another embodiment of the joint prothesis in an unexpanded condition.
Figure 6B:
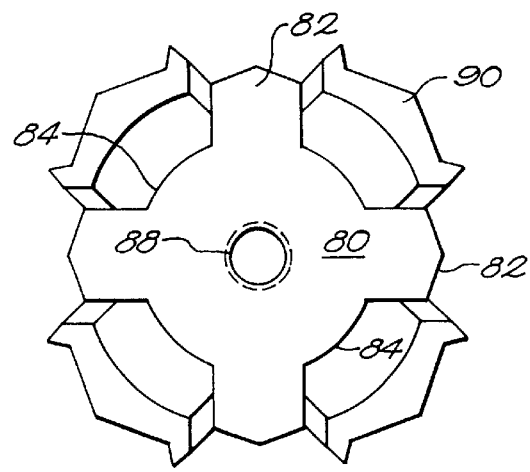
FIG. 6B is a bottom view of another embodiment of the joint prothesis in an expanded condition.

An alternate embodiment of the prosthesis system 10 is shown in FIGS. 6A and 6B. In this embodiment, the expander nut 80 includes opposed pairs of rotation inhibiting projections 82 and tine engaging sidewalls 84. The rotation inhibiting projections 82 are adapted to engage longitudinal slots provided on the stem member to prevent unwanted rotation of the expander nut. The expander nut 80 further includes a threaded central bore 88 for mating with a bolt member effective to draw the expander nut towards the proximal end of the prosthesis. In the embodiment shown in FIGS. 6A and 6B, as the bolt member is turned, the tine members 90 are expanded in a uniform fashion with respect to one another.

Figure 7:
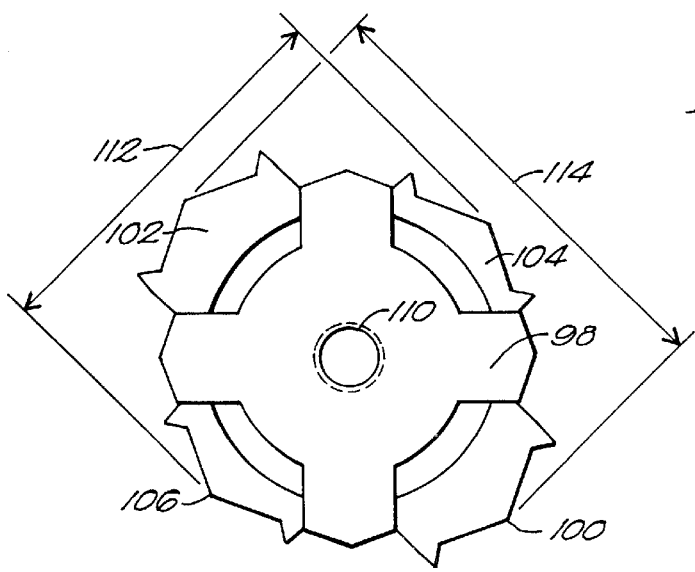
FIG. 7 is a bottom view of another embodiment of a joint prosthesis having expandable tine members of varying thicknesses.

Alternatively, as shown in FIG. 7, the prosthesis may be provided with tine members that have varying thicknesses. In this embodiment, the prosthesis includes an expander nut 98 and tine members 100, 102, 104 and 106 of varying thicknesses. As illustrated, tine members 100 and 102 are provided with thicker cross sections relative to tine members 104 and 106, forming a prosthesis with more than one effective diameter. The prosthesis includes a first, minor diameter 112, measured in a first direction about tine members 104 and 106. The first, minor diameter is preferably in the range of about 10 to 18 mm. A second, major diameter 114, is measured in a second direction substantially transverse to the first diameter 112 about tine members 100 and 102. The second, major diameter is preferably in the range of 13 to 23 mm. In this configuration, tine members 100 and 102 will be expanded, upon turning of a bolt member coupled to central bore 110, to a larger diameter relative to tine members 104 and 106. The thickness of the individual tine members in the minor diameter may range from 1to 3 mm. The thickness of the individual tine members in the major diameter may range from about 2 to 6 mm.

It is understood that various modifications can be made to the present invention without departing from the intended scope thereof. The entirety of all references noted herein is expressly incorporated by reference herein.

What is claimed is:

1. A bone prosthesis comprising:

an implantable elongate stem member of an artificial joint having a bore extending therethrough, the stem member having a proximal end including a joint motion surface adapted to receive a joint articulation member, and a distal end with at least one slot formed in the distal end, the at least one slot extending along at least a portion of the stem member in a longitudinal direction from the distal end towards the proximal end to form at least two tines at the distal end of the stem;

a bolt member disposable within the bore of the stem member, the bolt member having a proximal end and a distal end, wherein at least a portion of the bolt member proximate the distal end is threaded; and an expander nut including a perimeter having at least one stepped-in portion formed therein that is adapted to seat a tine, the stepped-in portion being effective to prevent rotation of the expander nut with respect to the stem and to cause side edges of adjacent tines to be offset, the expander nut being disposed between the tines and threadably matable with the distal end of the bolt member such that rotation of the bolt member in a first direction is effective to draw the expander nut towards the proximal end of the stem member to separate the tines at the distal end of the stem member and to define a cavity between the tines.

2. The bone prosthesis of claim 1, wherein the expander nut includes a threaded center bore that is coaxial with a longitudinal axis of the stem.

3. The bone prosthesis of claim 1, wherein the expander nut includes a minor diameter, measured in the a first direction, in the range of 8 to 16 mm.

4. The bone prosthesis of claim 3, wherein the minor diameter is the range of 8 to 16 mm and the major diameter is in the range of 10 to 18 mm.

5. The bone prosthesis of claim 1, wherein the slots formed on the distal end of the stem member form four expandable tine members.

6. The bone prosthesis of claim 5, wherein the tine members have different thicknesses.

7. The bone prothesis of claim 1, wherein the bolt member includes a head portion and a shaft that extends distally from the head portion.

8. The bone prosthesis of claim 1, wherein the cavity tapers outwardly from a distal end of the bore to the distal end of the stem member.

* * * * *